(12) United States Patent
Ayasse et al.

(10) Patent No.: US 8,703,084 B2
(45) Date of Patent: Apr. 22, 2014

(54) REMOVAL OF SULFUR COMPOUNDS FROM A GAS STREAM

(75) Inventors: Conrad Ayasse, Calgary (CA); Ahmed M. Shahin, Airdrie (CA); Alan Ayasse, Calgary (CA)

(73) Assignee: Archon Technologies Ltd., Calgary, Alberta (CA)

(*) Notice: Subject to any disclaimer, the term of this patent is extended or adjusted under 35 U.S.C. 154(b) by 48 days.

(21) Appl. No.: 13/399,710

(22) Filed: Feb. 17, 2012

(65) Prior Publication Data
US 2013/0217944 A1     Aug. 22, 2013

(51) Int. Cl.
*C01B 17/04* (2006.01)
*C01B 17/16* (2006.01)
*C10L 3/10* (2006.01)

(52) U.S. Cl.
USPC ............. 423/242.1; 423/244.01; 423/244.09; 423/244.1; 423/539; 423/564; 423/574.1; 48/127.3; 48/127.5; 48/127.7; 208/189; 208/208 R (58) Field of Classification Search
USPC ......... 423/242.1, 244.01, 244.09, 244.1, 539, 423/564, 574.1; 48/127.3, 127.5, 127.7; 208/189, 208 R
See application file for complete search history.

(56) References Cited

U.S. PATENT DOCUMENTS

| | | | | | |
|---|---|---|---|---|---|
| 3,752,877 | A | * | 8/1973 | Beavon | 423/244.1 |
| 4,426,369 | A | * | 1/1984 | Palm | 423/574.1 |
| 5,985,227 | A | * | 11/1999 | Immel et al. | 423/242.1 |
| 6,096,280 | A | * | 8/2000 | Ellenor et al. | 423/242.1 |
| 8,501,135 | B1 | * | 8/2013 | Ayasse et al. | 423/242.1 |

* cited by examiner

*Primary Examiner* — Timothy Vanoy
(74) *Attorney, Agent, or Firm* — D. Doak Horne; Gowling Lafleur Henderson LLP (57) ABSTRACT

A method and apparatus for eliminating COS and/or $CS_2$ from a hydrocarbon-containing feed stream, and further eliminating $H_2S$ from such feed stream or converting all sulfur species in such feed stream to $H_2S$ and $SO_2$ to allow for easy subsequent conversion of such $H_2S$ and $SO_2$ to elemental sulfur in a Claus reaction. The method comprises: (i) injecting water so that the feed stream contains greater than 10 vol % (water equivalent); (ii) passing the feed stream through catalyst means which hydrogenates COS and/or $CS_2$ to $H_2S$; (iii) injecting $O_2$ so that the stoichiometric ratio of $O_2$ to $H_2S$ is at least 0.5:1.0; (iv) passing the stream though a reaction zone having oxidation catalyst means which oxidizes $H_2S$ to elemental sulfur or $SO_2$ (depending on the amount of oxygen and water added); where the temperature of the reaction zone is above the elemental sulfur dew point.

33 Claims, 4 Drawing Sheets

REMOVAL OF SULFUR COMPOUNDS FROM A GAS STREAM

FIELD OF THE INVENTION

The present invention relates to a method and apparatus for removing or reducing certain sulfur species from an incoming gas stream that also contains combustible hydrocarbons and $H_2S$, and for further reducing or removing $H_2S$ from such incoming gas stream or alternatively readying said gas stream for being able to subsequently remove such $H_2S$ by a known processes thereby permitting such gas stream to be cleansed of such sulfur species.

BACKGROUND OF THE INVENTION

Many industrial gas streams are contaminated with sulfur compounds/species such as hydrogen sulphide ($H_2S$), sulfur dioxide ($SO_2$), carbonyl sulphide (COS), mercaptans (ie "RSH", where R represents an alkane, alkene, or other carbon-containing groups of atoms), and/or carbon disulphide ($CS_2$). For environmental or regulatory reasons it is typically mandated to remove or reduce the levels of such sulphur sulfur species in such industrial gas streams, such as in pipelines proximate to human habitation. It has been estimated that about forty percent or 2600 Tcf of the world's natural gas reserves are in the form of sour gas where $H_2S$ and $CO_2$ compositions exceed 10% of the raw produced sour gas. Other gas streams also contain sulfur species: for examples, refinery gas, in situ combustion produced gas, and coal and petroleum gasifiers.

A number of prior art processes currently exist to remove specifically the $H_2S$ from gas streams.

For example, one approach is subject the gas stream to an acid gas removal unit, which removes substantial amounts of $H_2S$ and CO2 from the $H_2S$ containing stream. The off-gas from the acid-gas removal unit is mainly $H_2S$ and $CO_2$. The sulfur from this off-gas stream is usually removed by the Claus reaction which produces saleable elemental sulfur. Specifically, the Claus process may be used for processing large volumes, and a liquid reduction-oxidation processes used for intermediate sour gas volumes, and $H_2S$ disposable scavengers for small volumes. However, these processes can be relatively expensive in capital and operating costs.

Below is a Review of Prior Art and Sulfur Species Chemical Reactions:

In the first step in the Claus process, about one third of the $H_2S$ present may be oxidized to $SO_2$. In the second step, remaining $H_2S$ and $SO_2$ are reacted in the presence of a Claus catalyst to form elemental sulfur in a series of Claus reactors according to Reaction 1:

$H_2S+\frac{3}{2}O_2 \rightarrow SO_2+H_2O$     1a.

$2H_2S+SO_2 \rightarrow 2H_2O+3S$ Claus reaction     1b.

The Claus reaction is limited by thermodynamic equilibrium and only a portion of the sulfur can be produced. Therefore, multiple stages with sulfur condensation between the stages are used to increase the sulfur recovery factor. However, the effluent gas from a series of reactors in a Claus plant can contain varying amounts of different compounds including sulfur vapour, $SO_2$, un-reacted $H_2S$, COS, and $CS_2$. Carbon disulphide is formed according to Reaction 2:

$CH_4+4S \rightarrow CS_2+2H_2S$ High temp. Claus furnace or combustion reaction     2.

Typically, this Claus plant effluent gas stream is burned with air to convert all sulfur-containing compounds in the stream to $SO_2$ before discharge into the atmosphere. As environmental requirements are become stricter, the $SO_2$ emission limit is being lowered, giving rise to the challenge of how to reduce or eliminate $SO_2$ emissions.

Another process for the oxidation of $H_2S$ to elemental sulfur is described in U.S. Pat. No. 4,197,277 by the following $H_2S$ Oxidation Reactions 3a and $H_2S+0.5O_2 \rightarrow S+H_2O$   $H_2S$ Partial oxidation     3a.

$H_2S+1.5O_2 \rightarrow SO_2+H_2O$   $H_2S$ Complete oxidation     3b.

According to the '277 patent, the $H_2S$-containing gas is passed with an oxygen-containing gas over a catalyst which comprises iron oxide and vanadium oxide as active materials and aluminum oxide as a support material. The catalyst described in the patent gives rise to at least a partial Claus equilibrium, so that $SO_2$ formation cannot be prevented. Similarly, U.S. Pat. No. 5,352,422 describes a process for oxidizing the un-reacted $H_2S$ in the Claus tail gas to elemental sulfur. The patent describes a catalyst prepared by impregnation of an iron containing solution or an iron/chromium-containing solution into several carriers followed by calcination in air at 500° C.

U.S. Pat. No. 4,818,740 discloses a catalyst for the $H_2S$ oxidation to elemental sulfur, the use of which is said to prevent the reverse Claus reaction to a large extent. The catalyst comprises a support of which the surface exposed to the gaseous phase does not exhibit any alkaline properties under the reaction conditions, while a catalytically active material is applied to this surface. A modification of the method disclosed in '740 is disclosed in European patent 409,353. This patent relates to a catalyst for the selective oxidation of sulfur-containing compounds to elemental sulfur, comprising at least one catalytically active material and optionally a support. The described catalyst exhibits substantially no activity towards the reverse Claus reaction under the reaction conditions.

The direct oxidation of $H_2S$ to elemental sulfur is known to take place on a wide range of catalysts. However, many of the catalysts experience a rapid deactivation and fouling due to a high level of carbon and/or sulfur deposits and irreversible sulphation of the catalyst surface. Alumina-based catalysts are particularly susceptible in this regard. U.S. patent application 2005/0100504 relates to a process for selective oxidation of $H_2S$ to elemental sulfur in the presence of an inert liquid medium to moderate the reaction temperature and to remove the sulfur from the reaction zone. The inert medium used in this application could be water, produced liquid sulfur, or any other liquid that is not substantially consumed under the reaction conditions. The oxidation reaction was carried out at a temperature in the range of from 120-160° C. and a high pressure preferably in the range of from 60-120 bars (absolute) in order to maintain the supplied liquid in the liquid form during the oxidation process to enable it to remove the sulfur from the reaction zone. Nevertheless, carrying the $H_2S$ oxidation reaction at temperatures below the sulfur dew point and high pressures can force the produced sulfur to deposit inside the catalyst pore structures.

The gas streams from different chemical processes may contain a range of sulfur-containing compounds such as, $H_2S$, $SO_2$, COS, $CS_2$ and RSH. Gases from combustion processes, such as in-situ combustion and coal or coke gasification may also contain CO, $CO_2$ and $H_2$. In the direct oxidation process, represented by Reaction 3a, oxygen is reacted with $H_2S$ over a catalyst to convert it to elemental sulfur. Because $SO_2$ and COS are not altered in the catalytic direct oxidation process, a pretreatment process of the gas feed stream is conducted to convert sulfur-containing compounds to $H_2S$ so that a higher sulfur removal efficiency can be achieved. U.S. Pat. Nos. 4,552,746 and 4,857,297 relate to a process for the oxidation of $H_2S$ to elemental sulfur in the presence of oxidation catalyst and a feed gas stream comprising less than 10 vol % water. The feed stream is pretreated to convert the sulfur-containing compounds to $H_2S$. The feed gas pretreatment could be accomplished in Reactions 4-7 by using, for example a dual hydrolysis/hydrogenation catalyst of cobalt or nickel/molybdenum on alumina to convert the undesirable components in the gas stream to $H_2S$ so that the stream would become amenable to direct oxidation:

Hydrogenation $RCH_2SH+H_2 \rightarrow H_2S+RCH_3$ Mercaptan hydrogenation  4.

$SO_2+3H_2 \rightarrow H_2S+2H_2O$ Sulfur dioxide hydrogenation  5.

$CS_2+4H_2 \rightarrow 2H_2S+CH_4$ Carbon disulfide hydrogenation  6.

$COS+4H_2 \rightarrow H_2S+CH_4+H_2O$ Carbonyl sulphide hydrogenation  7.

The rapid deactivation of the $H_2S$ direct oxidation catalyst was addressed by carrying out the oxidation reaction at a temperature above the sulfur dew point at the reaction conditions. Canadian patent 2,318,734 relates to a process for passing a hydrogen sulphide-containing gas stream mixed with the oxygen-containing stream over a catalyst comprising niobium oxide and a promoter on a titanium dioxide carrier. The stability of the catalyst was investigated in the presence of water and carbon dioxide and at a temperature above the sulfur dew point to slow the deactivation of the oxidation catalyst due to the sulfur deposition. The $H_2S$ conversion to elemental sulfur was greater than 90% and sulfur selectivity was greater than 85%. Although the presence of $CO_2$ in the feed gas stream increases the possibility of the COS formation (Reaction 11) during the $H_2S$ direct oxidation to elemental sulfur, the effluent gas was not analyzed for COS:

$H_2S+CO_2 \rightarrow COS+H_2O$  11.

Furthermore, the inventors of CA 2,318,734 and those of U.S. Pat. Nos. 4,552,746 and 4,857,297 apparently did not evaluate the performance of the disclosed $H_2S$ oxidation catalyst in the presence of a feed stream containing carbon monoxide, which undergoes side reactions during the $H_2S$ direct oxidation process to form COS:

CO Reactions $CO+S \rightarrow COS$  8.

$CO+H_2S \rightarrow COS+H_2$  9.

$3CO+SO_2 \rightarrow COS+2CO_2$  10.

X-Ray diffraction analysis of the disclosed catalyst showed a homogenous mixture of the oxides of Nb and Ti. The presence of Nb oxides in the catalyst increases the number of the Lewis acid sites on the Ti surface (Jih-Mirn Jehng and Israel E. Wachs, Catalysis Today, 8, 1, 1990). As a result, the catalyst could became inactive for the COS and/or $CS_2$ hydrolysis even at high temperature and in the presence of water (P. Grancher, C. Blanc, G. Guyot, M. Mathieu, J. Npugayrede, and J. Tessier, Inform. Chem., 199, 145, 1980).

Therefore, the concentration of COS and/or $CS_2$ in the product gas effluent of the above patents is expected to be substantial, and a post-treatment process would be required to convert the produced COS to $H_2S$, which in turn can be recycled to the $H_2S$ direct oxidation reactor to achieve a high sulfur removal efficiency. Such hydrolysis/hydrogenation pre- and/or post-treatment steps require additional capital and operating costs for the supply of hydrogen, which supply is lacking due to only providing, in accordance with the aforementioned patents (particularly U.S. Pat. Nos. 4,552,746 and 4,857,297) which stipulate that water in the feed gas stream comprise less than 10 vol % water.

SUMMARY OF THE INVENTION

In order to overcome the above problems foreseen with the methods and apparatus of U.S. Pat. Nos. 4,552,746, 4,857,297 and CA 2,318,734, namely the failure to eliminate concentrations of COS and/or $CS_2$ in the produced gas stream and the need for a post-treatment process to convert the COS to $H_2S$, the possible fouling of the catalyst, and the additional capital and operating costs for the supply of hydrogen for any hydrogenation reactions used in any pre-treatment processes, in a broad aspect the present invention advantageously provides a method and apparatus for overcoming such problems economically, using only addition of oxygen and water (and thus no need to supply hydrogen gas) which method substantially converts sulfur species present in an incoming gas stream to elemental sulfur or alternatively to $SO_2$ which can subsequently by means of a Claus reaction be easily then converted to elemental sulfur.

As used herein, "sulphur species" refers to one or more sulphur-containing compounds which high quantities are undesirable in an effluent stream. Such compounds include, but are not limited to, hydrogen sulphide (H2S), sulphur dioxide (SO2), carbonyl sulphide (COS), mercaptans (RSH), and carbon disulphide (CS2). As used herein, "sour gas" refers to gas containing more than 5.7 milligrams of H2S per cubic meter.

Specifically, the present invention, by utilizing water in the incoming stream or supplying additional quantities of water or steam to such incoming gas stream, is able to utilize such water or steam in the catalytic means provided to hydrolyze the water and hydrogenate the sulfur species present in the incoming gas stream to form $H_2S$, and subsequently by oxidation catalysts oxidize such $H_2S$ and any pre-existing $H_2S$ in the incoming gas stream to elemental sulfur or to $SO_2$ which can subsequently by means of a Claus reaction be easily then converted to elemental sulfur, thereby resulting in substantial elimination of such sulfur species from the produced gas stream. Typically, gas feed streams from sour gas wells contain sulfur species in sufficient quantities such that hydrogenation of such species to $H_2S$ requires that water or steam (water equivalent) be present in, or injected into such feed stream, such that the total of such water or steam (water equivalent) is in excess of 10% by volume of such feed stream. Of course, the amount of water or steam needed to be injected, if any, for the hydrolysis and hydrogenation reaction depends on the amount of water or steam originally present in the feed stream, and the amount of sulfur species needed to be hydrogenated.

Advantageously, such method avoids the need (and associated expense and equipment) to separately supply hydrogen gas for the hydrogenation of sulfur species in the gas stream, as was required in the prior art, including the pre-treatment method disclosed in U.S. Pat. Nos. 4,552,746, 4,857,297.

Accordingly, in a broad aspect the present invention comprises a method of reducing the amount COS and/or $CS_2$ in an incoming gas stream that also contains combustible hydrocarbons and H₂S, comprising:
  a. injecting, if necessary, molecular oxygen to said incoming gas stream so that the stoichiometric ratio of molecular oxygen to H₂S in said incoming gas stream is at least 0.5:1.0;
  b. injecting water or steam to said incoming gas stream, if necessary so that the gas stream contains water or steam greater than 10 vol % (water equivalent);
  c. providing a reaction zone comprising catalyst means comprising active sites suitable for hydrogenation of said COS and/or CS₂ to H₂S via hydrolysis of said injected water or steam, and a reaction zone comprising oxidation catalyst means for oxidation of H₂S to elemental sulfur or SO₂, wherein the temperature of each reaction zone is at or above the elemental sulfur dew point at the reaction pressure; and
  d. flowing said gas stream over said catalyst to produce an effluent stream;
  wherein the effluent stream comprises a reduced level of said COS and/or CS₂ species when compared to the incoming gas stream.

Advantageously, by providing water in excess of 10% vol. (water equivalent) when such water is mixed with the incoming gas stream, such water is thereby able to provide sufficient hydrogen to allow the catalyst means to effectively hydrogenate of the quantities of sulfur species typically present in hydrocarbon gas streams to produce H₂S through one or more of the following reactions:

CS₂+4H₂→2H₂S+CH₄ Carbon disulfide hydrogenation

COS+4H₂→H₂S+CH₄+H₂O Carbonyl sulphide hydrogenation

Thereafter, the H₂S may then, depending on the quantum of oxygen and water supplied in the process, be able to be directly oxidized to elemental sulfur through H₂S partial oxidation (reaction 3a above—H₂S+0.5O₂→S+H₂O), or via a complete oxidation to SO₂ (via reaction 3b above—H₂S+1.5O₂→SO₂+H₂O).

The step in the above method of partial oxidation of H₂S to elemental sulfur results in elimination of all sulfur species from the incoming stream. Specifically, wherein the incoming gas stream contains additional sulfur species, and wherein said water or steam is injected in sufficient quantity, and a flow rate through the reaction zone, and the quantity of said catalyst means is sufficient, to permit hydrogenation of substantially all of said COS and/or CS₂ to H₂S via said catalyst means, and thereafter oxidize substantially all of said H₂S to elemental sulfur upon injection of molecular oxygen if required, all such sulfur species can be removed.

In some conditions, however, depending on the concentration of H₂S and COS and/or CS₂ in the incoming stream, it may be more desirable to fully oxidize in the oxidation step the H₂S to SO₂, which will allow a subsequent Claus reaction to thereafter convert the so-formed SO₂ and remaining H₂S (which advantageously in the present method can be adjusted in the process to the preferred stoichiometric ratio of 2 H₂S:1 SO₂ for the subsequent Claus reaction) to elemental sulfur and water, via the following reaction, namely:

2H₂S+SO₂→2H₂O+3S

Such last step may be done via Claus, CrystaSulf, or other redox sulfur removal units. This may reduce or eliminate the need for an amine scrubber or H₂S burner.

In one embodiment of the above method of the present invention, the reaction zone for the hydrogenation and the reaction zone for oxidation are one and the same reaction zone.

In a further embodiment such method comprises first treating the incoming gas stream via a catalyst to hydrogenate COS and/or CS₂ to H₂S, and subsequently subjecting the resulting stream to a direct oxidation catalyst to oxidize H₂S to elemental sulphur or SO₂.

In a further refinement of the above method, water is introduced in liquid form, and gas to liquid water ratio in the incoming gas stream is in the range of from 10 to 5000 NL of gas per kg of water.

In a further refinement, water is introduced as steam, and gas to steam ratio in the incoming gas stream is in the range of from 10 to 5000 NL of gas per kg of steam (water equivalent).

In a further embodiment the water/oxygen levels in the incoming gas stream are adjusted such that effluent stream from the reaction zone comprising oxidation catalyst means comprises H₂S and SO₂ in a ratio of from about 1:1 to about 3:1, and more preferably in the optimum stoichiometric ratio for a subsequent Claus reaction, namely a ratio of about 2:1.

The catalysts employed comprise a metal oxide and/or sulphide deposited or mixed with one or more refractory metal oxides. The present process may employ any catalysts suitable for the hydrolysis of COS and/or CS₂ to H₂S, and for the oxidation of H₂S to elemental sulfur or SO₂. The oxidation catalyst may comprise an oxide and/or sulphide form of one or more metals deposited or mixed with one or more refractory metal oxides. The metal oxides and/or sulphides include, but are not limited to, oxides and/or sulphides of V, Cr, Mn, Fe, Co, Ni, Cu, Nb, Mo, Tc, Ru, Rh, Pd, Hf, Ta, W, Re, Os, Ir, Pt, Au, La, Ce, Pr, Nd, Pm, Sm, Eu, Gd, Tb, Dy, Ho, Er, Tm, Yb, Lu, Bi, and any suitable combinations thereof. The refractory metal oxides include, but are not limited to, Al, Ti, Si, Zr, and any suitable combinations thereof. The first catalyst may include any oxidation catalyst suitable for the selective oxidation of H₂S to elemental sulfur. Such oxidation catalysts are known in the art. For example, they may comprise an oxide and/or sulphide form of one or more metals. The second catalyst may be a hydrolysis catalyst suitable for the hydrolysis of COS and/or CS₂ to H₂S. The second catalyst may be of a higher basicity than the first catalyst and may comprise one or more metal oxides. Examples of such catalysts include, but are not limited to, Al₂O₃, TiO₂, Cu/Al₂O₃, Co&Mo/Al₂O₃, and suitable combinations thereof. The first catalyst and second catalyst may be utilized in the presence of water or water vapour under the same reaction conditions.

As noted above, the hydrogenation and oxidization reactions are carried out above the dew point of elemental sulfur, to avoid fouling the catalysts, to allow the sulfur to be carried away. At atmospheric pressure, the dew point of sulfur is approximately 150° C. Thus in embodiments where the pressures are atmospheric or higher, the temperature of the reaction zone is in the range of from about 150° C. to about 400° C., such temperatures, of course, being above the dew point temperature of sulfur for the pressure being used, which results in a pressure in the reaction zone is in the range of from about atmospheric pressure to about 500 psig.

In a preferred embodiment, the incoming gas stream is flowed over the oxidation catalyst at a gas hourly space velocity of 100 to 10,000 hr-1, which allows sufficient time for the hydrogenation and oxidative reactions to occur.

Because the hydrogenation Reactions 4-7 which take place in the method of the present invention form quantities of H₂S, and considering additional quantities of H₂S quantities may be originally present in the feed stock, typically greater quantities of oxidation catalyst than hydrogenation/hydrolysis catalyst will be needed in the method of the present invention. In preferred embodiments, the ratio of the oxidation catalyst to the hydrolysis catalyst is in the range of from about 0.5 to about 10 to 1, depending on the quantity of $H_2S$ originally present in the feed stock, the amount of sulfur species, and which of CS2 and/or COS and their respective quantities are originally present in the feed stock.

The reaction zone may comprise a first catalytic zone for hydrogenation and a second catalytic zone comprises an $H_2S$ oxidation catalyst. The reaction zone may be a vertical reaction zone, having a top catalytic zone and a bottom catalytic zone, the top zone comprising the oxidation catalyst and the bottom zone comprising the hydrolysis catalyst, and the feed stream enter firstly the bottom, and exit via the top. Alternatively for a vertical reaction zone, the top zone may comprise the hydrogenation catalyst and the bottom zone comprising the oxidation catalyst, and the feed stream enter firstly the top, and exit via the bottom.

Alternatively, the reaction zone may comprises a catalytic zone(s) comprising a mixture of a first catalyst and a second catalyst.

In the preferred embodiment, the reaction conditions within the first catalytic zone where hydrogenation occurs, and the second catalytic zone occurs are each carried out at a temperature in the range of from ambient to 400° C., a pressure in the range of from atmospheric to 500 psig, and at a gas hourly space velocity in the range from 100 to 10,000 hr-1. Alternatively, only one of the first catalytic zone or second catalytic zones may be carried out under these conditions.

In a preferred embodiment of the above method, effluent from the first catalytic zone is cooled to below the dew point of sulfur, and preferably cooled to room temperature, to allow separation of sulfur therefrom before said effluent is subsequently supplied to the second catalytic zone comprising the $H_2S$ oxidation catalyst.

In a further preferred embodiment, the stream produced from the first catalytic zone where hydrogenation occurs is mixed with molecular oxygen in the form of pure oxygen (or less preferably air which undesirably contains small amounts of $CO_2$) before it is supplied to the second catalytic zone where direct oxidation of $H_2S$ occurs.

It should be emphasized that the reaction zone may be in a single reactor, with oxygen and water being injected into the reaction zone where hydrogenation and oxidation occur.

Alternatively, the reactions of hydrogenation and oxidation may take place in separate catalytic beds or even separate reactors. Accordingly, in such alternative embodiment, the method of the present invention comprises a method of reducing the amount COS and/or CS2 in an incoming gas stream that also contains combustible hydrocarbons and $H_2S$, and COS and/or $CS_2$, the method comprising:

a. injecting water or steam to said incoming gas stream, if necessary, so that the gas stream contains sufficient water or steam to allow hydrolysis of said water or steam and hydrogenation of said amounts of COS and/or $CS_2$ to $H_2S$;

b. providing catalyst means comprising active sites suitable for said hydrolysis of water and hydrogenation of said COS and/or $CS_2$ to $H_2S$, and passing said incoming stream through said catalyst means, at a temperature at or above the elemental sulfur dew point at the reaction pressure, thereby forming a treated stream;

c. injecting, if necessary, molecular oxygen to said treated stream so that the stoichiometric ratio of molecular oxygen to $H_2S$ in said treated stream is at least 0.5:1.0;

d. providing a reaction zone having oxidation catalyst means comprising active sites suitable for oxidation of $H_2S$ to elemental sulfur or $SO_2$, wherein the temperature of the reaction zone is at or above the elemental sulfur dew point at the reaction pressure; and e. passing said treated stream through said reaction zone to form an effluent stream; and wherein said effluent stream comprises a reduced level of said COS and/or $CS_2$ species when compared to the incoming gas stream.

In most embodiments, due to the concentration of sulfur species in the feed stream, water or steam is present in said incoming stream provided to said catalyst means at a volume in excess of 10% vol. (water equivalent).

In the above method, the oxygen is preferably added to said treated stream at a stoichiometric ratio of molecular oxygen to $H_2S$ equal to or greater than 1.5:1.0.

Again, the injection rates of said water and/or oxygen are adjusted such that the effluent stream from the reaction zone comprises $H_2S/SO_2$ in a ratio of about 2:1.

Similarly, where the oxygen and water injection rates are adjusted so that the oxidation catalytic reaction is a full oxidation of $H_2S$ to $SO_2$, in a preferred embodiment the so-formed SO2 and remaining unoxidized $H_2S$ are further reacted in the presence of a Claus catalyst to form elemental sulfur.

In another aspect of the invention, the invention comprises an apparatus for carrying out the above method. More particularly, in another aspect of the invention, an apparatus for the removal of COS and/or $CS_2$ from a hydrocarbon-containing feed stream comprising $H_2S$, and COS and/or $CS_2$, is provided, comprising:

(i) reactor means, comprising a hydrogenation catalyst for catalyzing the hydrogenation of said COS and/or $CS_2$ to $H_2S$, and an oxidation catalyst capable of catalyzing the oxidation of the $H_2S$ to elemental sulfur or $SO_2$;

(ii) an incoming feed stream inlet, in fluid communication with said reactor means, adapted for conveying said feed stream to the reactor means;

(iii) a water inlet, adapted to allow water to be introduced into said feed stream entering said reactor means;

(iv) an outlet from said reactor, adapted for conveying an effluent gas stream away from the reactor.

In a preferred embodiment of the apparatus of the present invention, such apparatus comprises molecular oxygen injection means, for injecting said molecular oxygen in the form of oxygen gas, or less preferably air, into said reactor prior to said incoming gas stream flowing to said oxidizing catalyst.

To be able to adjust the rate of oxygen injected relative to the rate of feed gas entering, or the rate of water being injected relative to the rate of feed gas entering the reaction zone(s), mass flow controllers may be provided, capable of controlling the flow of any one of (i) the rate of water injection; (2) the rate of oxygen injection; and/or (3) the feed stream flow rate.

In a preferred embodiment, the apparatus further comprises a heat exchanger capable of heating the incoming gas stream.

In a still further embodiment, the apparatus further comprises a gas chromatograph for analyzing the effluent gas stream.

In a yet still further embodiment, the oxidation catalyst comprises metal compounds in the oxide and/or sulfide form.

This summary does not necessarily describe the entire scope of the present invention. Other aspects, features and advantages of the invention will be apparent to those of ordinary skill in the art upon review of the following description of specific embodiments of the invention.

DETAILED DESCRIPTION OF THE INVENTION

The present disclosure provides embodiments of a process for reducing the amount of sulfur species in a gas stream, which does not entail addition of hydrogen gas, but rather makes use of water (or steam) in the feed stream which through catalysts is hydrolyzed and such catalyst further acts to hydrogenate various sulfur species in the feed stream to $H_2S$. Oxygen, and oxidizing catalysts are subsequently used to produce elemental sulfur which can be removed, or an exhaust gas containing an $H_2S/SO_2$ ratio of about 2:1, which is can be fed to Claus, CrystaSulf, or other redox sulfur removal units.

$H_2S$-containing streams suitable for the present processes include, but are not limited to, light hydrocarbons such as methane, ethane, or propane; natural gas; associated gas from oil production; gases produced from oil sand refining, e.g. coker gas; gases produced from the Toe-to-Heel-Air-Injection process (THAI™), or other in-situ combustion processes; coal or oil gasification processes; inert gases such as nitrogen, helium or carbon dioxide, and oxidizable gases such as, carbon monoxide, hydrogen and any combinations thereof.

In certain processes according to the present disclosure a suitable amount of air or a molecular oxygen-containing gas is introduced into an $H_2S$-containing gas stream along with water in the vapour or liquid state, and the resulting mixture directed to an $H_2S$ direct oxidation reactor. The water, or the water equivalent in the case of steam, need typically be greater than 10 vol % of the total feed gas volume for typical incoming feed streams, in order to provide the necessary hydrogen for the hydrogenation of the sulfur species within the feed stream to be hydrogenated to $H_2S$. The concentration of the oxygen in the molecular oxygen-containing stream may be adjusted depending on the concentration of the $H_2S$ in the $H_2S$-containing stream. The oxygen-containing gas may be, but is not limited to, air, oxygen, or mixtures thereof. In embodiments of the present process the ratio of molecular $O_2$ to $H_2S$ may be slightly above the stoichiometric ratio of 0.5. Preferably the ratio is in the range of from about 0.5 to about 2, such as from about 0.6 to about 1. If desired, an excess molecular $O_2$ can be adjusted to produce $SO_2$, so that the exhaust effluent contains an $H_2S/SO_2$ ratio suitable for feeding to downstream redox reactors. For example, the $H_2S/SO_2$ ratio may be about 2:1.

The addition of water to the feed stream of an $H_2S$ direct oxidation reactor may have various functionality:

a. Water may hydrolyze COS and $CS_2$ that can be present in the feed gas stream and/or formed during the direct oxidation of $H_2S$ to elemental sulfur and/or $SO_2$ inside the reactor (Reactions 13 and 14):

Hydrolysis Reactions $$COS + H_2O \rightarrow H_2S + CO_2 \text{ COS hydrolysis (reverse of Reaction 10)} \quad 13.$$

$$CS_2 + 2H_2O \rightarrow 2H_2S + CO_2 \text{ } CS_2 \text{ hydrolysis} \quad 14.$$

b. Water in the presence of $H_2S$ in the gas stream may reduce sulphation of the $H_2S$ oxidation catalyst surface, in particular alumina and titania based catalysts [R. K. Kerr, H. G. Paskall and N. Ballash, Energy Process, 40 (1977), and Z. M. George, Can. J. Chem. Eng., 56, 711 (1977)]. The sulphation of alumina and titania based catalysts can increase the strength of the Lewis acid sites on the catalysts surface and consequently reduce their activities toward COS and/or $CS_2$ hydrolysis and reduce the efficiency of $H_2S$ direct oxidation to elemental sulphur;

c. Water can reduce the condensation of the produced sulfur such as in the catalyst pores which may improve the durability of the catalyst; and d. Water may reduces the sulfur contact time on the catalytic bed and consequently eliminate certain side reactions, such as Reactions 8 and 15:

$$S + O_2 \rightarrow SO_2 \quad 15.$$

In embodiments of the present process, the $H_2S$ direct oxidation (Reactions 3a and 3b) and COS and $CS_2$ hydrolysis reactions (Reactions 13 and 14) take place in the presence of water and at a temperature higher than the sulfur dew point under the reaction conditions.

The present disclosure provides an apparatus for implementing a process as described herein.

The apparatus comprises a gas-stream inlet, a reactor, and an outlet. The inlet is suitable for conveying a gas stream comprising a sulfur species to the reactor. The reactor is suitable for the oxidation of a sulfur species to elemental sulfur and contains an oxidation catalyst capable of catalyzing the oxidation of the sulfur species to elemental sulfur. The oxygen and water may be introduced to the reactor via the inlet or may be introduced though alternative means. The outlet is adapted for conveying an effluent gas stream wherein the effluent gas stream comprising less of the sulfur species than the inlet gas stream.

In an embodiment of the present process, an $H_2S$-containing gas stream and air or molecular oxygen are supplied to a reaction zone comprising an oxidation catalyst in the presence of water. The oxidation catalyst comprises active sites suitable for $H_2S$ oxidation to elemental sulfur and for COS and/or $CS_2$ hydrolysis to $H_2S$. The $H_2S$ oxidation reaction and/or hydrolysis of COS and/or $CS_2$ can be conducted in a down flow reactor, a slurry bubble column, or any other suitable reactor operates at a temperature in the range of from ambient to about 400° C., a pressure of up to about 1500 psig, and a gas hourly space velocity in the range of from about 100 to about 10,000 $hr^{-1}$.

Figure 1:
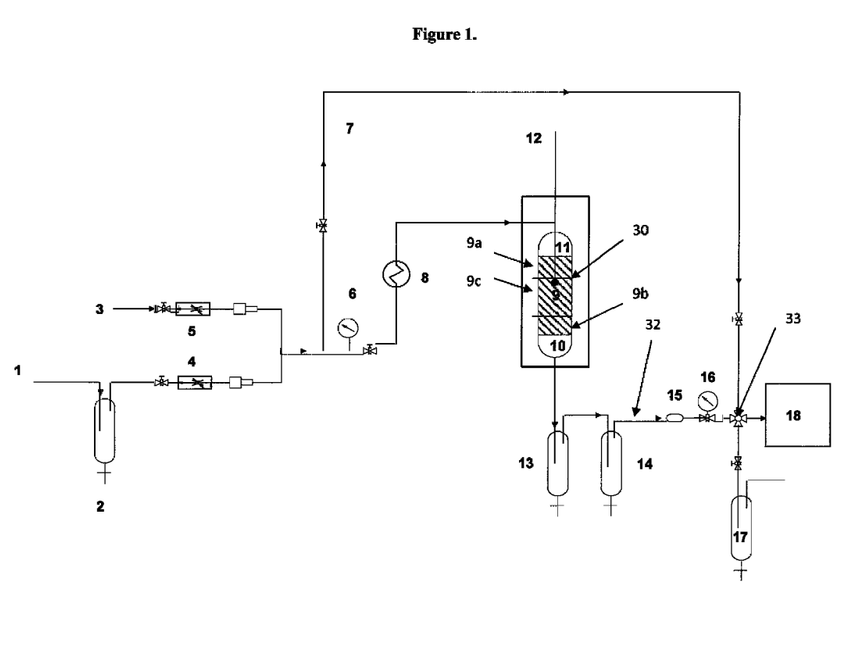
FIG. 1 is a schematic of an apparatus for direct oxidation of $H_2S$.

This embodiment may be implemented in an apparatus according to FIG. 1, which shows a schematic of a pilot process and an embodiment of the method of the present invention. The direct oxidation may conducted in a down-flow reactor 30. The reactor may comprise a single reaction zone 9 containing an appropriate amount oxidation catalyst such as 10.4 liters of an alumina supported bismuth and copper catalyst. The catalyst may be enclosed between two inert-particle zones 10 and 11 respectively. The apparatus has an inlet feed stream 1. Water may be added to the stream by any appropriate means (not shown). In this apparatus the stream 1 passes through a liquid collector 2 to separate liquid hydrocarbon droplets from the feed gas. The flow of the feed stream 1 may be controlled by a mass flow controller 4. The temperature and pressure of the stream may also be controlled as appropriate. For example, when used in an exemplary process for the direct oxidation of $H_2S$ the temperature of the stream was at ambient and the pressure at 18 psig. Air 3 may be mixed with the feed stream 1 prior to the heat exchanger 8, and its flow may be controlled via a mass flow controller 5. The feed stream 1 may enter a heat exchanger 8 to bring the feed stream temperature to the desired reaction temperature. The pressure of the inlet feed stream 1 may be monitored by a pressure gauge 6, and the combined inlet and air feed stream may be analyzed for the $H_2S/O_2$ ratio. The temperature of the oxidation reactor 30 can be sensed and recorded by a thermocouple 12. The produced fluid may be cooled to separate the produced sulfur from the gas phase in separators 13 and 14. A micro-filter 15 can be mounted on the outlet effluent line 32 to prevent the deposition of sulfur in the back pressure control valve 16. The composition of the produced gas may be analyzed periodically (e.g. at 30 minute intervals). This may be done by a gas chromatograph 18 which can be equipped with an automated stream selection valve 33. The produced stream may be passed through a sodium hydroxide solution 17 to absorb un-reacted $H_2S$.

Water supplied to the reaction zone 9 may serve as an internal coolant and can be in the vapour or liquid form, preferably in vapour form. Water absorbs heat released by exothermic oxidation reaction and may maintain the reaction temperature fairly constant and suitable for COS and/or $CS_2$ hydrolysis. If water is supplied in vapour form, the water vapour content in the feed stream is preferably adjusted to produce a gas mixture containing water vapour greater than 10 vol % of the total volume of the feed stream. If the water is present in liquid form, the volume of the feed gas to the weight of the supplied water is preferably in the range of from about 10 to about 5000 NL of gas/kg of water. The $H_2S$-containing stream and water can be supplied to the reaction zone 9 separately or co-mixed.

The amount of molecular oxygen entering via line 3 may be adjusted to achieve the highest conversion of $H_2S$ to elemental sulfur and to produce a gas effluent comprising a suitable $H_2S/SO_2$ ratio such as about 2:1. An effluent comprising gas, water and sulfur can be removed from the reaction zone and then cooled to room temperature. Liquid water entraining fine dispersed sulfur particles may then separated from a gaseous stream. A gaseous stream comprising $H_2S/SO_2$, preferably in a ratio of about 2:1, can be supplied to a Claus or other redox type process for further oxidation of $H_2S$ to elemental sulfur if desired. Produced solid sulfur may be separated from the liquid water via, for example, a phase separation. Alternatively, the process may be operated to minimize the total sulfur compounds in the effluent, which can then be burned.

In a variation of the present process, the reaction zone 9 can comprise a mixture of a first catalyst and a second catalyst. The first catalyst may include any oxidation catalyst suitable for the selective oxidation of $H_2S$ to elemental sulfur. Such oxidation catalysts are known in the art. For example, they may comprise an oxide and/or sulphide form of one or more metals. The second catalyst may be a hydrolysis catalyst suitable for the hydrolysis/hydrogenation of COS and/or $CS_2$ to $H_2S$. The second catalyst may be of a higher basicity than the first catalyst and may comprise one or more metal oxides. Examples of such catalysts include, but are not limited to, $Al_2O_3$, $TiO_2$, $Cu/Al_2O_3$, $Co\&Mo/Al_2O_3$, and suitable combinations thereof. The first catalyst and second catalyst may be utilized in the presence of water or water vapour under the same reaction conditions.

In a variation of the present process, the reaction zone 9 can comprise a top catalytic zone 9a and a bottom catalytic zone 9b in series. The use of two catalytic zones 9a, 9b in series can be useful in the case of a feed stream containing high concentrations of COS and/or $CS_2$, such as streams from combustion processes. The top catalytic zone 9a may comprise a catalyst that has activity for COS and/or $CS_2$ hydrolysis. It may be possible to transfer the effluent from the top catalytic zone 9a to the bottom catalytic zone 9b without any interstage cooling. The bottom catalytic zone 9b may comprise an oxidation catalyst suitable for the oxidation of $H_2S$ to elemental sulfur. The bottom zone 9b may comprise further catalysts such as those suitable for the hydrolysis of COS and/or $CS_2$ to $H_2S$.

In a variation of the present process, the reaction zone 9 can comprise a top catalytic zone 9a and a bottom catalytic zone 9b in series, wherein the top catalytic zone 9a comprises an oxidation catalyst suitable for $H_2S$ oxidation to elemental sulfur and $SO_2$ and the bottom catalytic zone 9b comprises a hydrolysis catalyst suitable for the hydrolysis of COS and/or $CS_2$ to $H_2S$. In a variation of the present process, the reaction zone 9 can comprise a top catalytic zone 9a, a middle catalytic zone 9c, and a bottom catalytic zone 9b. The use of multi-catalytic zones can be useful in the case of a feed stream containing high concentrations of $H_2S$, COS and/or $CS_2$. The top catalytic zone 9a can comprise a COS and/or $CS_2$ hydrolysis catalyst to hydrolyze COS and/or $CS_2$ to $H_2S$. The middle catalytic zone 9c may comprise an $H_2S$ oxidation catalyst to oxidize $H_2S$ to elemental sulfur and $SO_2$. The bottom catalytic zone 9b may exclusively comprise a COS and/or $CS_2$ hydrolysis catalyst to hydrolyze the formed COS and/or $CS_2$ to $H_2S$. The effluent from the top catalytic zone 9a may be sent to the middle catalytic zone 9c without interstage cooling. The effluent from the middle catalytic zone 9c may be transferred to the bottom zone 9b without interstage cooling.

While the catalytic zones 9a, 9b, 9c may be contained in a single reactor, in a variation of the present process the $H_2S$ partial oxidation and COS and/or $CS_2$ hydrolysis reactions are carried out in two or more separate reactors containing mono or multi catalytic zones.

Figure 2A:
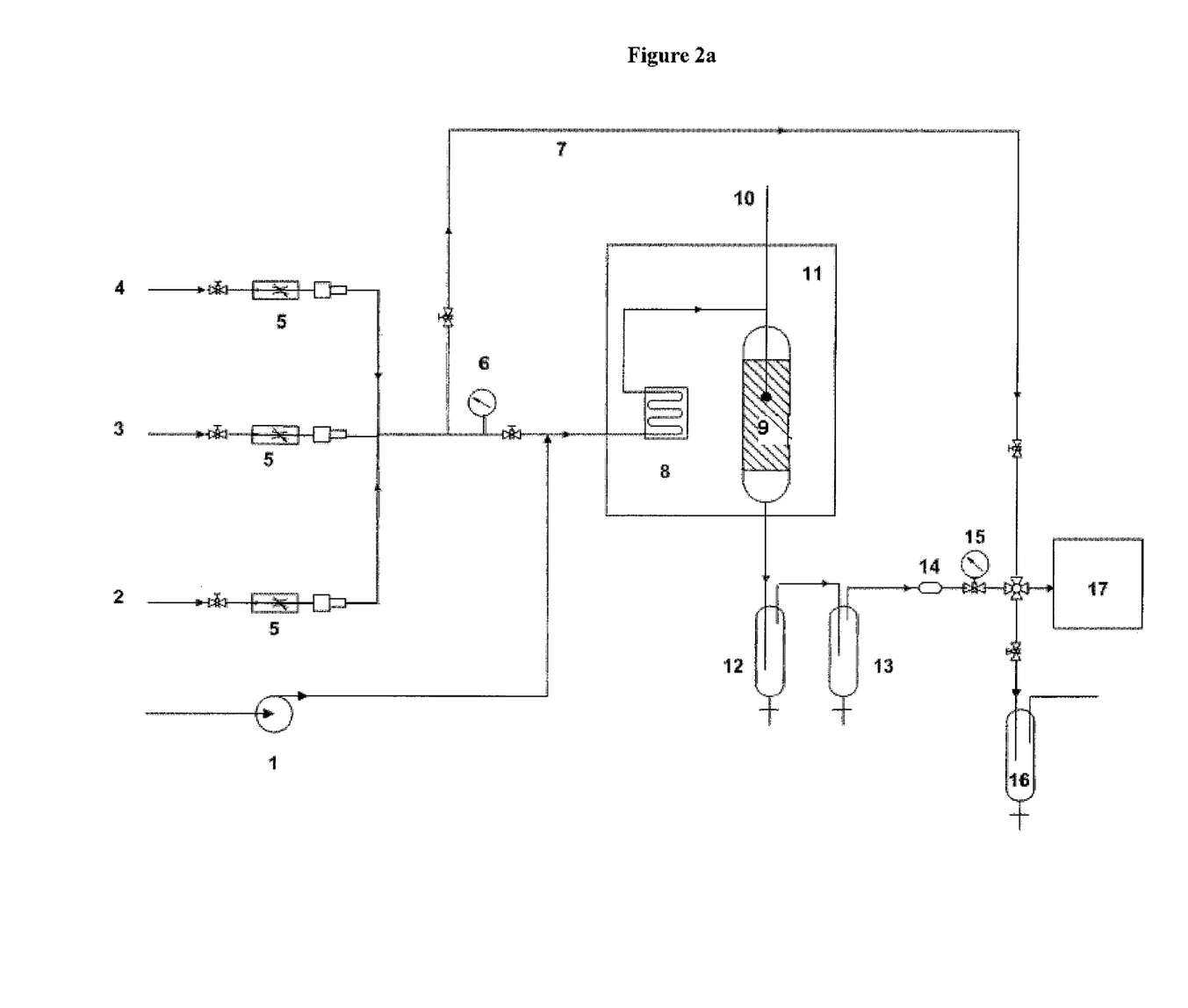
FIG. 2a is a schematic of an apparatus utilizing a single reactor apparatus for direct oxidation of $H_2S$ comprising a pump suitable for adding water.
Figure 2B:
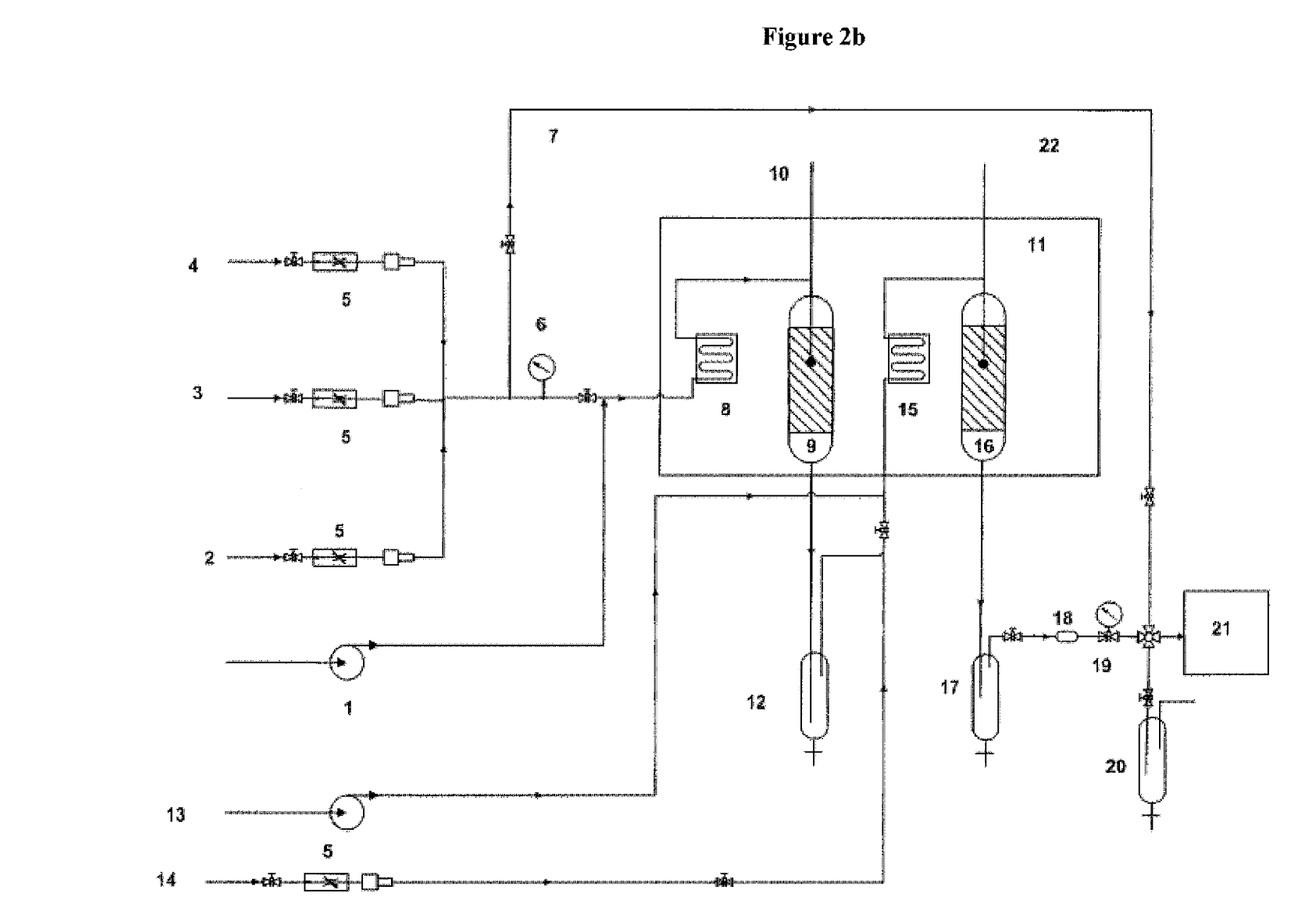
FIG. 2b is a schematic of an apparatus utilizing a dual reactor apparatus for direct oxidation of $H_2S$ comprising pumps suitable for adding water.

In a variation of the present invention shown in FIG. 2b, such invention relates to a process for recovering sulfur from an $H_2S$ containing stream is conducted in a first reactor and a second reactor. The process may include contacting an $H_2S$ containing stream, molecular oxygen, and water with one or more catalysts contained in a first reactor comprising mono or multi catalytic zones. The molecular oxygen concentration in the feed stream may be adjusted in order to produce the desired (e.g. minimal) amount of $SO_2$ in the produced effluent from the first reactor. Gas effluent may be removed from the first reactor and can be cooled to condense water and sulfur. Liquid water comprising fine sulfur particles may be separated from a gaseous stream comprising un-reacted $H_2S$, COS and/or $CS_2$ and trace $SO_2$. A second feed stream comprising a gas mixture of the first reactor product gas mixture, molecular oxygen, and water may be contacted with one or more catalysts contained in a second reactor comprising mono or multi catalytic zones. Gas effluent can be removed from the second reactor and may be cooled to separate water and sulfur. The molecular oxygen concentration in the second feed stream may be adjusted to achieve the desired (e.g. highest) conversion of $H_2S$ to elemental sulfur. It can be desirable to produce a gas effluent from the second reactor comprising an $H_2S/SO_2$ ratio of about 2:1. The catalysts contained in the first and second reactors may have activity for catalyzing the $H_2S$ oxidation to elemental sulfur and the hydrolysis of COS and/or $CS_2$ to $H_2S$.

The $H_2S$ partial oxidation and $COS/CS_2$ hydrolysis reactions may be conducted in one or more reactors comprising mono or multi catalytic zones at temperatures above the dew point of the sulfur, a pressure up to about 1000 psig, a gas hourly space velocity in the range of from about 100-1000 $hr^{-1}$, and in the presence of water in the form of liquid or vapour.

The present processes can be utilized on any suitable $H_2S$-containing stream without the necessity of any pre or post hydrogenation and/or hydrolysis of COS and/or $CS_2$. The produced effluent contains low COS and/or $CS_2$ content. Preferably the $H_2S/SO_2$ ratio in the effluent is about 2:1 and is thus ready for redox-type processing for further desulfurization of the $H_2S$ containing streams.

FIG. 2a shows a schematic of the laboratory equipment used in direct $H_2S$ oxidation Examples 3 to 4. The catalytic oxidation of $H_2S$ to elemental sulfur was performed in a fixed bed laboratory reactor 9 with and without the presence of water 1. The system consisted of a gas feeding section 2 ($H_2$, $N_2$, $CH_4$, $CO_2$ and CO mixture), 3 ($H_2S/N_2$) and 4 (air), and a downflow reactor containing a single catalytic zone 9, an oven, 11, a gas pre-heating zone 8, and two-stage gas-liquid separators (12 and 13). The downflow reactor 9 was a thick-walled 316 stainless steel tube of 25 mm internal diameter and 255 mm length. The upper and bottom zones of the downflow reactor 9 were packed with inert particles and the $H_2S$ oxidation catalyst was enclosed between the zones of inert particles. The temperature of the oxidation reactor 9 was recorded by a thermocouple 10. The reaction system included mass flow controllers 5 for supplying the various gases and an HPLC pump 1 for optionally adding water. The outlet stream passed through a micro-filter 14 and the pressure of the reactor 9 was controlled by a back-pressure control valve 15 mounted on the outlet gas stream. The produced fluid was then cooled to separate the produced sulfur from the gas phase in separators (12 and 13). The composition of the inlet 7 and outlet gas streams were monitored by a gas chromatograph 17 equipped with 4 channels. The product gas was passed through a sodium hydroxide solution 16 to absorb the un-reacted $H_2S$.

FIG. 2b shows a schematic of the laboratory equipment used in the direct oxidation reaction according to Example 6. The $H_2S$ catalytic oxidation was performed in a fixed bed reactor 9 in the presence of water 1. The experimental set-up of the first reactor is similar to that employed in Example 3 and 4. However, the outlet fluids from reactor 9 entered a first sulfur separator 12 to remove sulfur from the effluent tail gas. The outlet gas from the sulfur separator 12 was mixed with water 13 and air 14 and then supplied to a second pre-heating zone 15. The outlet stream from the pre-heating zone 15 was then fed to a second oxidation reactor 16 and then to a second sulfur separator 17. The temperature of the second oxidation reactor was recorded by a thermocouple 22. The outlet stream from the second sulfur separator 17 passed through a micro-filter 18 and then through a back-pressure control valve 19. The composition of the outlet stream was analyzed every 30 minutes by a gas chromatograph 21 and the product gas was passed through a sodium hydroxide solution 20 to absorb un-reacted $H_2S$.

Figure 3:
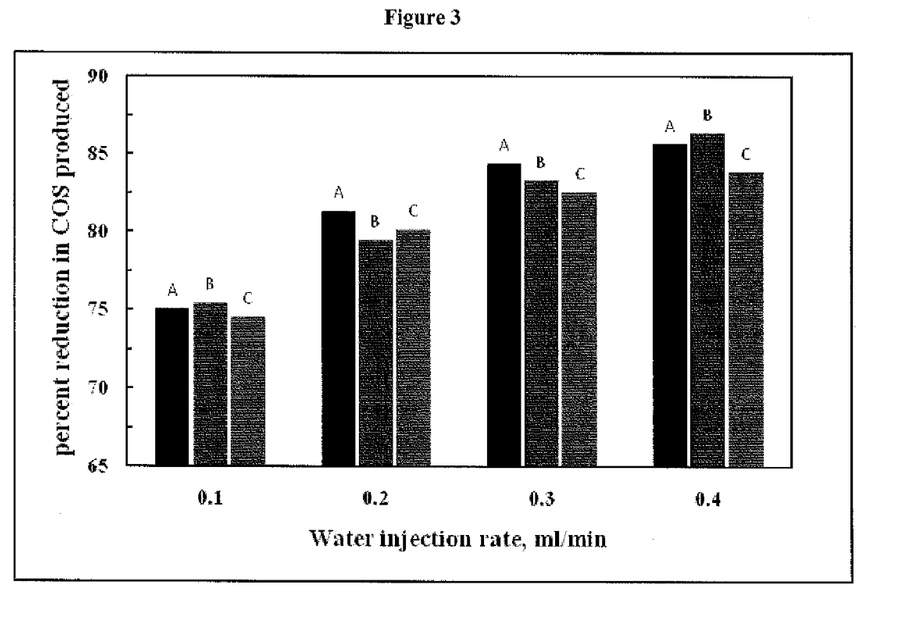
FIG. 3 is a graph showing the water injection rate to percent reduction in COS for a process according to an embodiment of the present disclosure.

FIG. 3 shows the effect of pressure and water concentration on the quantity of COS produced with the laboratory equipment of FIG. 2. Compared with the absence of injected water, where A represents the percentage reduction in COS produced at 100 psig for water, B at 80 psig, and C at 60 psig for additions of 0.1, 0.2, 0.3 and 0.4 ml/minute.

Figure 4:
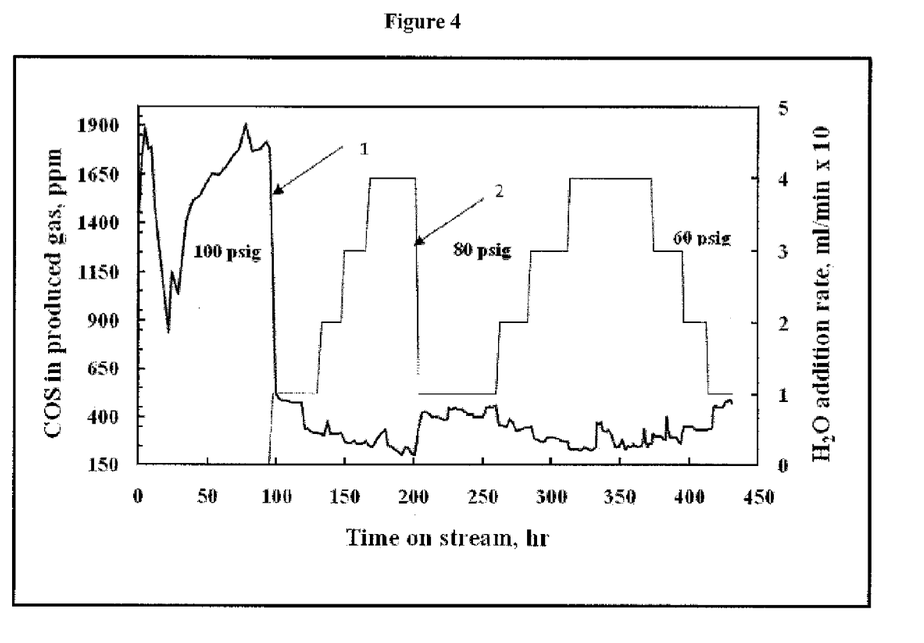
FIG. 4 is a graph showing water addition rate to the amount of COS in a produced gas for a process according to an embodiment of the present disclosure.

FIG. 4 shows the reduction of effluent COS by water addition. The number 1 indicates the ppm COS concentration in the effluent and the number 2 the ml/min of water added.

It is contemplated that any embodiment, aspect, example, method, composition, or element discussed in this specification may be implemented or combined in any suitable manner with any other embodiment, aspect, example, method, composition, or element.

Unless defined otherwise, all technical and scientific terms used herein have the same meaning as is commonly understood by one of ordinary skill in the art to which this invention belongs. Unless otherwise specified, all patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference. Citation of references herein is not to be construed nor considered as an admission that such references are prior art to the present invention.

The invention includes all embodiments, modifications and variations substantially as hereinbefore described and with reference to the examples and figures. It will be apparent to persons skilled in the art that a number of variations and modifications can be made without departing from the scope of the invention as defined in the claims. Examples of such modifications include the substitution of known equivalents for any aspect of the invention in order to achieve the same result in substantially the same way.

Embodiments of the invention are illustrated, in part, by the following non-limiting methods and examples

Example 1

Comparative

This Example used the apparatus shown in FIG. 1. No water was added to the gas stream and the gas produced had the composition given in Table 1.

TABLE 1

| THAI ™ Process gas composition (in situ petroleum combustion process) | |
|---|---|
| Component | % by volume |
| $H_2$ | 3.60 |
| $O_2$ | 0.00 |
| $N_2$ | 74.41 |
| $CH_4$ | 4.31 |
| CO | 1.50 |
| $CO_2$ | 14.94 |
| Ethane | 0.55 |
| $H_2S$ | 0.40 |
| Propane | 0.28 |

In order to operate the downflow reactor 9 isothermally, the temperature of the outer surface of the reactor 9 was controlled with electrical heating elements and the reaction temperature was maintained at ~230° C. The gas hourly space velocity of the feed gas was about 1500 $hr^{-1}$ and the $O_2/H_2S$ ratio was 0.5 and varied based on the $H_2S$ concentration in the feed gas. The average pressure of the inlet gas was 18 psig, while the average pressure of the outlet gas was 4 psig. The compositions of the feed and produced gases were monitored via a micro gas chromatograph equipped with 4 channels As shown in FIG. 4, after 2 weeks on stream, the average $H_2S$ conversion was 60% of the total inlet $H_2S$ and sulfur selectivity was approximately 45%. The activity of the catalyst toward $H_2S$ oxidation to elemental sulfur decreased rapidly due to the carbon and sulfur deposits. The amounts of carbon and sulfur deposited on the catalyst surface were 4.5% and 8.3%, respectively Example 2

The fouled catalyst from Example 1 was used in this Example. Approximately 20 ml of the fouled catalyst collected from Example 1 were used in this Example without regeneration or any other pre-treatment. The fouled catalyst was loaded into a downflow laboratory reactor 9 (FIG. 2a) and then placed in an oven. Two different gas streams shown below were used to prepare a synthetic direct oxidation raw inlet feed gas of the composition shown in Table 2, which is similar to that used in the THAI™ Process direct oxidation field pilot of FIG. 1 and Example 1:
($H_2S/N_2$); ($CH_4$, $CO_2$, CO, $H_2$ and $N_2$). Air was added to the synthetic mixture.

TABLE 2

Synthetic feed gas composition.

| Component | % by volume |
|---|---|
| $H_2$ | 3.03 |
| $O_2$ | 0.00 |
| $N_2$ | 77.86 |
| $CH_4$ | 4.31 |
| CO | 1.07 |
| $CO_2$ | 13.24 |
| $H_2S$ | 0.49 |

The temperature of the catalyst bed was increased slowly to 220° C. at a constant flow of the dry gas mixture and at atmospheric pressure. At a temperature of 220° C., the pressure of the reactor 9 was increased to the reaction pressure of 100 psig and the gas hourly space velocity of the inlet feed stream was set at 1000 $hr^{-1}$. The out-flow lines were maintained at 150° C. to avoid the sulfur plugging in the lines. The produced fluids entered a hot separator where sulfur was collected. A secondary cold separator was employed to separate the sulfur from the gas phase, and a 2μ stainless steel filter was used to capture the trace of the sulfur before the back pressure control valve. Gaseous and liquid effluents were continuously removed from the reactor 9. After 96 hours of operation the $H_2S$ conversion and sulfur selectivity without water addition were calculated and are shown in Table 3 as Example 2a. Water was then mixed with the feed gas in the pre-heating zone at a rate of 0.4 gm/min and the results are also shown in Table 3 as Example 2b. Comparing Example 2a and Example 2b it can be seen that there are advantages to adding water in the direct oxidation of $H_2S$ to elemental sulfur with fouled catalyst. The presence of water, with all other conditions unchanged, increased sulfur yield from 45% to 62.6% and reduced problematic COS from 1600 ppm to 245 ppm.

The addition of water to the $H_2S$ direct oxidation reactor comprising a fouled alumina supported bismuth and copper catalyst hydrolyzed a good deal of the formed COS to $H_2S$ and decreased its concentration in the produced effluent substantially. The molecular oxygen supplied to the oxidation reaction was consequently adjusted to achieve a higher conversion of $H_2S$ to elemental sulfur and to produce a gas effluent comprising $H_2S/SO_2$ in a ratio of about 2:1. While not wishing to be bound by theory it is believed that the oxygen reacted selectively with the $H_2S$ and, therefore, increased the sulfur selectivity from 52.3% to 78.5% upon adding water to the oxidation reaction.

The above $H_2S$ direct oxidation experiments revealed that upon using a dry $H_2S$-containing stream as a feed gas, CO side reactions were present and produced undesirable high level of COS.

To test the effect of water level, water rates were set at 0.3, 0.2 and 0.1 ml/min.

TABLE 3

Wet and dry Direct Oxidation of $H_2S$.

| Reaction parameters | Single reactor, example 2a* | Single reactor, Example 2b | Two reactors, Example 5 |
|---|---|---|---|
| Catalyst | Fouled alumina supported bismuth and copper | Fouled alumina supported bismuth and copper | Reactor A: Fouled alumina supported bismuth and copper Reactor B: Fresh alumina supported bismuth and copper |
| Reaction temperature, ° C. | 220 | 220 | 220 |
| Reaction pressure, psig | 100 | 100 | 100 |
| Water rate, ml/min | dry | 0.4 | 0.4 |
| Feed GHSV, $h^{-1}$ | 1000 | 1000 | 1000 (Reactor A) |
| Total $O_2/H_2S$ | 0.76 | 0.88 | 0.98 |
| Total $H_2S$ conversion, % | 86 | 79.7 | 90.4 |
| Average $SO_2$ produced, ppm | 440 | 520 | 287 |
| Average COS produced, ppm | 1600 | 245 | 316 |
| Sulfur yield, % | 45 | 62.6 | 78.1 |
| $H_2S/SO_2$ ratio | 2.0 | 2.0 | 2.0 |

*Dry Direct Oxidation of $H_2S$:

Example 3

The reaction conditions used in Example 3 were similar to the reaction conditions employed in Example 2b, except that the pressure of the reaction was reduced to a pressure of 80 psig.

Example 4

The reaction conditions used in Example 4 were similar to the reaction conditions employed in Example 2, except that the pressure of the reaction was reduced to a pressure of 60 psig.

As shown in Table 4, it was found that higher operating pressures can be beneficial in terms of higher sulfur yields.

TABLE 4

The effect of pressure on the Direct Oxidation of $H_2S$ to elemental sulfur

| Reaction parameters | Example 2b | Example 3 | Example 4 |
|---|---|---|---|
| Catalyst | Fouled alumina supported bismuth and copper | | |
| Reaction temp., ° C. | 220 | | |
| Feed GHSV, $h^{-1}$ | 1000 | | |
| Water rate, ml/min | 0.4 | | |

TABLE 4-continued

The effect of pressure on the Direct Oxidation of $H_2S$ to elemental sulfur

| Reaction parameters | Example 2b | Example 3 | Example 4 |
|---|---|---|---|
| Reaction pressure, psig | 100 | 80 | 60 |
| Total $O_2/H_2S$ | 0.88 | 0.94 | 1.1 |
| Total $H_2S$ conversion, % | 79.7 | 72.9 | 70.8 |
| Average $SO_2$ prod., ppm | 520 | 565 | 765 |
| Average COS prod., ppm | 245 | 231 | 275 |
| Sulfur yield, % | 62.6 | 56 | 49.2 |
| $H_2S/SO_2$ ratio | 2.0 | 2.0 | 2.0 |

Considering FIG. 4, at 100 psig, when there was no water addition, produced COS was at a maximum of 1910 ppm. When water was added at 0.1 ml/min, the COS rapidly decreased to 480 ppm and then decreased further to a minimum of 230 ppm when water was increased to 0.4 ml/min. When the pressure was decreased to 80 psig with 0.1 ml/min water addition, the concentration of produced COS increased, compared with the 100 psig result, indicating that COS removal is moderately benefited by higher pressures. Again at 80 psig, the COS concentration was reduced by increasing the level of added water.

Effect of Water Concentration

While not wishing to be bound by theory it is believed that the reactions of CO with the $H_2S$ present in the feed stream, and with the sulfur produced from the oxidation reaction, substantially reduced the sulfur yield. Therefore, an excess amount of water was required to simultaneously hydrolyze the produced COS to $H_2S$ according to Reaction 12. From FIG. 3, the reduction of COS increases with higher water concentrations. As shown in Reaction 1, the stoichiometric conversion of pure $H_2S$ to elemental sulfur requires only 0.5 moles of oxygen. However, in the presence of oxidizable carbon molecules such as carbon monoxide and methane, higher quantities of oxygen are needed. With a dry feed gas, excess oxygen produces excess quantities of $SO_2$ (Reaction 2) and of COS (Reaction 9). Because water co-injected with the feed gas hydrolyzes COS (reverse of Reaction 12), the molecular oxygen level supplied to the $H_2S$ direct oxidation reactor can safely be increased above the stoichiometric quantity, thereby achieving a higher sulfur yield while still controlling COS formation.

Example 5

As noted from Example 2, mixing water at a rate of 0.4 ml/min with the $H_2S$ containing stream in the pre-heating zone prior to the oxidation reactor decreased the COS level from 1600 ppm (using a dry feed stream) to 245 ppm. Using an $O_2/H_2S$ ratio of 0.88, the total $H_2S$ conversion was 79.7%, sulfur yield was 62.6%, unconverted $H_2S$ was 1034 ppm, and $SO_2$ concentration was 520 ppm, giving the desired $H_2S/SO_2$ ratio of about 2. In order to further improve the total $H_2S$ conversion, the $O_2/H_2S$ ratio was increased from 0.88 to 1. However, the $SO_2$ concentration in the produced gas increased and accordingly, COS concentration increased via Reaction 9.

Example 5 demonstrates a variation on Example 2 by increasing the $H_2S$ conversion and sulfur yield through the use of higher $O_2/H_2S$ ratios without increasing the COS production. Two identical fixed bed reactors (Reactor A and Reactor B) were employed for oxidizing $H_2S$ to elemental sulfur and hydrolyzing formed COS to $H_2S$, simultaneously. Reactor A and reactor B are identical to the reactor employed in Example 2. Both of Reactor A and reactor B were placed in an oven at a temperature of 220° C. Reactor A was loaded with 20 ml of the fouled alumina supported bismuth and copper catalyst, whereas, Reactor B was loaded with 20 ml of a fresh alumina supported bismuth and copper catalyst. Reactor A was operated at reaction conditions similar to the reaction conditions employed in Example 2, except that the molecular oxygen concentration was adjusted to achieve a low conversion of $H_2S$ to COS and $SO_2$. Water at a rate of 0.4 ml/min was mixed with molecular oxygen and an $H_2S$ containing gas stream of a composition similar to the composition of the feed stream employed in Example 2. The inlet fluid mixture was pre-heated to the desired reaction temperature in the pre-heating zone prior to Reactor A and the total gas hourly space velocity available for Reactor A was 1000 hr$^{-1}$. The $H_2S$ oxidation reaction was conducted at 220° C. and a pressure of 100 psig. The fluid produced from Reactor A entered a cold separator to condense and separate water and sulfur from the gaseous phase before it was supplied to Reactor B. The composition of the gas effluent produced from Reactor A was analyzed and the total $H_2S$ conversion was 60.8%. The low $H_2S$ conversion may be attributed to the low oxygen level in the feed gas. The sulfur selectivity was 88.6%, COS produced was 210 ppm and $SO_2$ produced was 130 ppm.

The gas effluent produced from Reactor A was then mixed with molecular oxygen containing stream (air) and water at a rate of 0.4 ml/min in the pre-heating zone prior to Reactor B. Molecular oxygen level was adjusted to achieve a high $H_2S$ conversion to elemental sulfur. The gas effluent produced from Reactor B was cooled to separate water and sulfur from the gaseous phase. Subsequently, the composition of the gas phase from Reactor B was analyzed.

Table 3 shows the results of the $H_2S$ direct oxidation to elemental sulfur and COS hydrolysis to $H_2S$ processes according to Example 2 and Example 5 utilizing a single reactor and two reactors. Utilizing two oxidation reactors in the presence of an excessive amount of water increased the sulfur yield from 62.6% (according to Example 2d) to 78.1 (according to Example 5), while still maintaining an $H_2S/SO_2$ ratio of 2.

Use of examples in the specification, including examples of terms, is for illustrative purposes only and is not intended to limit the scope and meaning of the embodiments of the invention herein. Numeric ranges are inclusive of the numbers defining the range. In the specification, the word "comprising" is used as an open-ended term, substantially equivalent to the phrase "including, but not limited to," and the word "comprises" has a corresponding meaning.

The invention claimed is:

1. A method for reducing an amount COS and/or $CS_2$ in a gas stream that also contains combustible hydrocarbons and $H_2S$, comprising:
   a. providing in a reaction zone catalyst means comprising active sites suitable for hydrolysis of said COS and/or $CS_2$ to $H_2S$ via reaction with water or steam present in or injected in said gas stream and without hydrogenation to form $H_2S$, said reaction zone or a further reaction zone comprising oxidation catalyst means for oxidation of $H_2S$ to $SO_2$, wherein the temperature of said reaction zone or zones is at or above the elemental sulfur dew point at the reaction pressure;
   b. flowing said gas stream over said catalyst means and producing an effluent stream;
   c. ensuring that the molar ratio of molecular oxygen to $H_2S$ in the reaction zone is at least 0.5:1.0 and that at least quantities of $H_2S$ are oxidized to $SO_2$; and d. ensuring that said gas stream contains said water or steam at levels greater than 10 vol % (water equivalent) to allow hydrolysis of said amounts of COS and/or $CS_2$ to $H_2S$.

2. The method of claim 1, wherein said water or steam is present in or is further provided to said gas stream in sufficient quantity to permit said conversion of substantially all of said COS and/or $CS_2$ originally in or subsequently formed in said gas stream or effluent stream to $H_2S$.

3. The method of claim 1, wherein said gas stream contains additional sulfur species, and wherein said water or steam is injected in sufficient quantity and at a flow rate through the reaction zone, and the quantity of said catalyst means is sufficient, to permit conversion of substantially all of said sulfur species including COS and/or $CS_2$ to $H_2S$ via said catalyst means, and upon addition of molecular oxygen if required into said reaction zone, oxidize substantially all of said $H_2S$ to $SO_2$.

4. The method of claim 1, wherein said reaction zone for the hydrolysis and the reaction zone for oxidation are one and the same reaction zone.

5. The method of claim 1, wherein said effluent stream, after said $CS_2$ and/or COS therein are converted to $H_2S$ via said hydrolysus with said water or steam, subsequently undergoes a Claus type reaction wherein said oxidation catalyst converts said $H_2S$ and formed $SO_2$ to water and elemental sulfer.

6. The method according to claim 1, 2, or 3, wherein water is introduced in liquid form, and gas to liquid water ratio in the gas stream is in the range of from 10 to 5000 NL of gas per kg of water.

7. The method according to claim 1, 2, or 3 wherein water is introduced as steam to the gas stream, and the resulting gas to steam ratio in the gas stream is in the range of from 10 to 5000 NL of gas per kg of steam (water equivalent).

8. The method according to claim 1, 2, or 3, further comprising the step of ensuring, by injection of oxygen if necessary into said reaction zone, that the molar ratio of molecular oxygen to $H_2S$ in at least portions of said reactor zone is at least 1.5:1.0.

9. The method according to claim 1, 2, or 3 wherein water, steam, and or oxygen is injected into the reaction zone such that the effluent stream from the reaction zone comprises $H_2S/SO_2$ in a molar ratio of about 2:1.

10. The method according to claim 1 wherein the hydrogenating catalyst and/or the oxidizing catalyst comprises a metal oxide and/or sulphide deposited or mixed with one or more refractory metal oxides.

11. The method according to claim 1 wherein the temperature of the reaction zone is in the range of from about 150° C. to about 400° C.

12. The method according to claim 1 wherein incoming gas stream is flowed over the oxidation catalyst at a gas hourly space velocity of 100 to 10,000 $hr^{-1}$.

13. The method according to claim 1 wherein the pressure in the reaction zone is in the range of from about atmospheric pressure to about 500 psig.

14. The method according to claim 1 wherein the ratio of the oxidation catalyst to the hydrolysis catalyst is in the range of from about 0.5 to about 10:1.

15. The method according to claim 1 wherein the reaction zone comprises a top catalytic zone and a bottom catalytic zone, the top zone comprising the oxidation catalyst and the bottom zone comprising the hydrolysis catalyst, and the gas stream passes from bottom to top.

16. The method according to claim 1 wherein the reaction zone comprises a top catalytic zone and a bottom catalytic zone, the top zone comprising the hydrolysis catalyst and the bottom zone comprising the oxidation catalyst and the gas stream passes from top to bottom.

17. The method as claimed in claim 1, where the reaction zone comprises a catalytic zone(s) comprising a mixture of a first catalyst and a second catalyst.

18. The method as claimed in claim 17, wherein the first catalyst has activity for COS and/or $CS_2$ hydrogenation to $H_2S$.

19. The method as claimed in claim 17, wherein the second catalyst has activity for $H_2S$ oxidation to $SO_2$.

20. The method as claimed in claim 17, wherein the second catalyst to the first catalyst ratio is in the range of from 0.5 to 10:1.

21. The method as claimed in claim 1, where the reaction zone is substantially vertical and comprises a catalytic zone (s) comprising a top catalyst and a bottom catalyst.

22. The method as claimed in claim 21, wherein the top catalyst has activity for $H_2S$ oxidation and $SO_2$, and the bottom catalyst has activity for COS and/or CS2 hydrolysis to $H_2S$, and the gas stream passes from bottom to top.

23. The method as claimed in claim 21, wherein the top catalyst has activity for COS and/or $CS_2$ hydrolysis to $H_2S$, and the bottom catalyst has activity for $H_2S$ oxidation to $SO_2$, and the gas stream passes from top to bottom.

24. The method as claimed in claim 1, wherein the reaction zone comprises a first catalytic zone for COS and/or $CS_2$ to $H_2S$, and a second catalytic zone comprises an $H_2S$ oxidation catalyst.

25. The method as claimed in claim 24, wherein the reaction conditions within the first catalytic zone and/or the second catalytic zone include: a temperature in the range of from ambient to 400° C., a pressure in the range of from atmospheric to 500 psig, and using a gas hourly space velocity in the range from 100 to 10,000 hr−1.

26. The method as claimed in claim 24, wherein effluent from the first catalytic zone is cooled to below the dew point of sulfur and said sulfur separated therefrom before said effluent is subsequently supplied to the second catalytic zone comprising said $H_2S$ oxidation catalyst.

27. The method as claimed in claim 24, wherein $H_2S$ and the stream produced from the first catalytic zone is mixed with molecular oxygen before it is supplied to the second catalytic zone.

28. The method as claimed in any one of claim 24, 25, 26, or 27, wherein the catalyst(s) in the first catalytic zone and the second catalytic zone comprises active sites suitable for and for hydrolyzing COS to $H_2S$ and for oxidation of $H_2S$ to $SO_2$.

29. A method of reducing the amount COS and/or $S_2$ in a gas stream that also contains combustible hydrocarbons and $H_2S$, the method comprising:
  a. injecting water or steam to said incoming gas stream, if necessary, so that the gas stream contains sufficient water or steam to allow hydrolysis of said water or steam and hydrogenation of said amounts of COS and/or $CS_2$ to $H_2S$;
  b. providing catalyst means comprising active sites suitable for said hydrolysis of water and hydrogenation of said COS and/or $CS_2$ to $H_2S$, and passing said incoming stream through said catalyst means, at a temperature at or above the elemental sulfur dew point at the reaction pressure, thereby forming a treated stream;
  c. injecting, if necessary, molecular oxygen to said gas stream so that the molar ratio of molecular oxygen to $H_2S$ in said gas stream is at least 0.5:1.0;
  d. providing a reaction zone having oxidation catalyst means comprising active sites suitable for oxidation of H$_2$S to elemental sulfur or SO$_2$, wherein the temperature of the reaction zone is at or above the elemental sulfur dew point at the reaction pressure; and e. passing said treated stream through said reaction zone to form an effluent stream; and wherein said effluent stream comprises a reduced level of said COS and/or CS$_2$ species when compared to the incoming gas stream.

30. The method as claimed in claim 29, wherein said water or steam is present in said incoming stream provided to said catalyst means, at a volume in excess of 10% vol. (water equivalent).

31. The method as claimed in claim 29, wherein said molecular oxygen is added to said treated stream at a molar ratio of molecular oxygen to H$_2$S equal to or greater than 1.5:1.0.

32. The method according to claim 29 wherein injection rates of said water and/or oxygen are adjusted such that said effluent stream from the reaction zone comprises H$_2$S/SO$_2$ in a ratio of about 2:1.

33. The method as claimed in claim 32, wherein H$_2$S and SO$_2$ in said effluent stream are further reacted in the presence of a Claus catalyst to form elemental sulfur.

* * * * *